(12) United States Patent
Tynan, Jr. et al.

(10) Patent No.: US 9,372,147 B2
(45) Date of Patent: Jun. 21, 2016

(54) PLATEN TAPE TEST METHOD AND DEVICE

(71) Applicants: John Kinch Tynan, Jr., Port Huron, MI (US); Shaun Robert Graham, Columbia, SC (US)

(72) Inventors: John Kinch Tynan, Jr., Port Huron, MI (US); Shaun Robert Graham, Columbia, SC (US)

(73) Assignee: INTERTAPE POLYMER CORP., Sarasota, FL (US)

( * ) Notice: Subject to any disclaimer, the term of this patent is extended or adjusted under 35 U.S.C. 154(b) by 530 days.

(21) Appl. No.: 13/765,977

(22) Filed: Feb. 13, 2013

(65) Prior Publication Data

US 2013/0213127 A1    Aug. 22, 2013

Related U.S. Application Data

(60) Provisional application No. 61/600,127, filed on Feb. 17, 2012.

(51) Int. Cl.
*G01N 19/04*    (2006.01)

(52) U.S. Cl.
CPC ........ *G01N 19/04* (2013.01); *G01N 2203/0476* (2013.01)

(58) Field of Classification Search
CPC ...................................... G01N 19/04
USPC ............................ 73/150 A, 150 R
See application file for complete search history.

(56) References Cited

U.S. PATENT DOCUMENTS

| | | | |
|---|---|---|---|
| 2008/0202254 A1* | 8/2008 | Deng et al. ...................... | 73/827 |
| 2011/0037687 A1* | 2/2011 | Akamatsu et al. ............... | 345/87 |
| 2012/0103081 A1* | 5/2012 | Hoshino ..................... | 73/150 A |
| 2012/0123700 A1* | 5/2012 | Tsaur .............................. | 702/41 |

OTHER PUBLICATIONS

5500 Series Advanced materials testing systems, 2007, Instron, pp. 1-16.*
Peel Adhesion of Pressure Sensitive Tape, May 2007, Harmonized International Standard, Ed. 3, pp. 101-1-101-10.*
Pressure Sensitive Tape Council (PSTC); "Peel Adhesion of Pressure Sensitive Tape"; PSTC 101; Harmonized International Standart; pp. 101-1 through 101-10; http://www.pstc.org/files/public/101.pdf; (May 2007).
CA, Office Action; Canadian Patent Application No. 2,805,577 (Aug. 3, 2015).

* cited by examiner

*Primary Examiner* — Hezron E Williams
*Assistant Examiner* — David Z Huang
(74) *Attorney, Agent, or Firm* — Thompson Hine LLP (57) ABSTRACT

A device for testing adhesive tape including a sample holder located in a first plane and a movable platen having a major surface located in a plane perpendicular to the plane in which the sample holder is located. The platen and the sample holder each have an edge adjacent to the edge of the other, where the platen and the sample holder are moveable with respect to each other such that the movement of the platen with respect to the sample holder separates the adjacent edges and thereby applies a load to a length of tape that is secured to the surface of a sample in the holder and secured to the surface of the platen during testing.

20 Claims, 10 Drawing Sheets

PLATEN TAPE TEST METHOD AND DEVICE

This application claims priority to U.S. Provisional Patent Application 61/600,127, filed on Feb. 17, 2012, and entitled Platen Tape Test Method and Device, the entire contents of which are incorporated by reference herein.

TECHNICAL FIELD

The present invention relates to methods and devices for evaluating the adhesion strength of tapes.

BACKGROUND OF THE INVENTION

The invention relates to a test method and device for determining the time to adhesive failure of carton sealing tape when applied to a corrugated or recycled linerboard samples and the like. The test is designed to measure the abilities of different sealing tapes to adhere to different substrates such as corrugated and linerboard. The adhesion of a sealing tape for a particular substrate varies with a number of different factors including temperature, humidity, and the fiber content and the method to manufacture of the substrate. For example, the surfaces of similar fiber boards may also exhibit considerable variation between mills, batches and within batches. Common adhesive tape testing methods test tensile, 180° peel, and shear. The method measures and plots load and time.

SUMMARY

One embodiment of the invention is a device for testing adhesive tape including a sample holder located in a first plane and a movable platen having a major surface located in a plane perpendicular to the plane in which the sample holder is located. The platen and the sample holder each have an edge adjacent to the edge of the other, where the platen and the sample holder are moveable with respect to each other in a direction perpendicular to the adjacent edges such that the movement of the platen with respect to the sample holder separates the adjacent edges and thereby applies a load to a length of tape that is secured to the surface of a sample in the holder and secured to the surface of the platen during testing.

Another embodiment of the invention is a device for testing tape including a sample holder located in a first plane and a movable platen having a major surface located in a plane perpendicular to the plane in which the sample holder is located. The platen and the sample holder each having an edge adjacent and parallel to the edge of the other, and the platen and the sample holder are moveable with respect to each other such that the movement of the platen with respect to the sample holder separates their adjacent edges and thereby applies a load to a length of tape that is secured to the surface of a sample in the holder and secured to the surface of the platen during testing. The device includes a control panel for selecting the load applied to the tape during the test, wherein the load can be varied, and the device includes a switch and a timer, where the switch signals the timer to being recording the elapsed time, and the device records or displays the time to failure when the tape fails.

Another embodiment of the invention is a method for testing a tape, including the steps of adhering a length of tape to a sample, a portion of the length of tape extending from the sample, placing the sample in a sample holder, the sample holder being located in a plane and having an edge adjacent an edge of a movable platen, the sample holder and the platen being located perpendicular to one another along their adjacent edges, adhering the portion of the tape extending from the sample to the platen, and actuating the platen to apply a load to the tape, contemporaneously measuring the time that elapses between applying the load to the tape and the time the tape fails.

DETAILED DESCRIPTION

Figure 1:
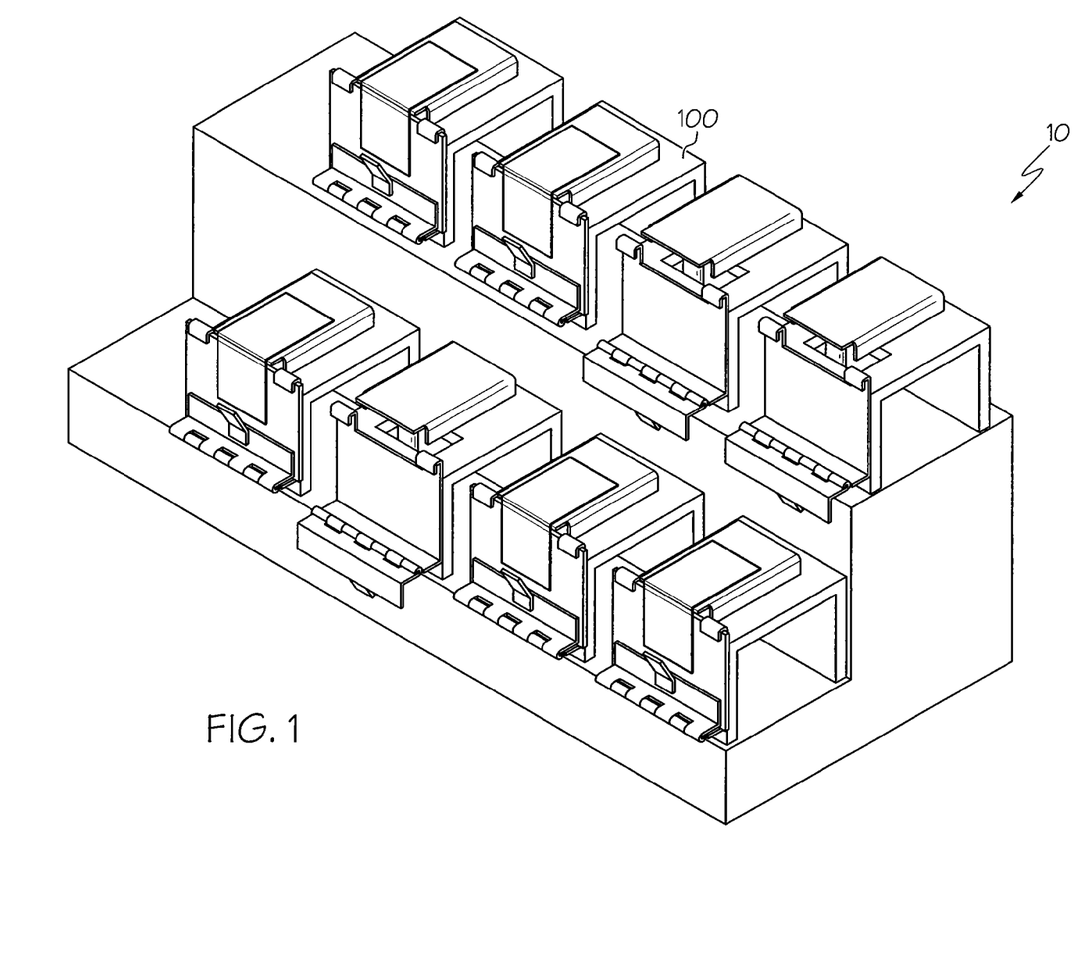
FIG. 1 is a front perspective view of an array of platen testers.

Referring now to the drawings, FIG. 1 depicts a testing array 10 including a plurality of platen testers 100. Testing array 10 may include any number of platen testers 100, and in one embodiment, platen testers 100 may be arranged in pairs to form an array 10 of sixteen testers 100 arranged in eight pairs of testers 100.

Figure 2:
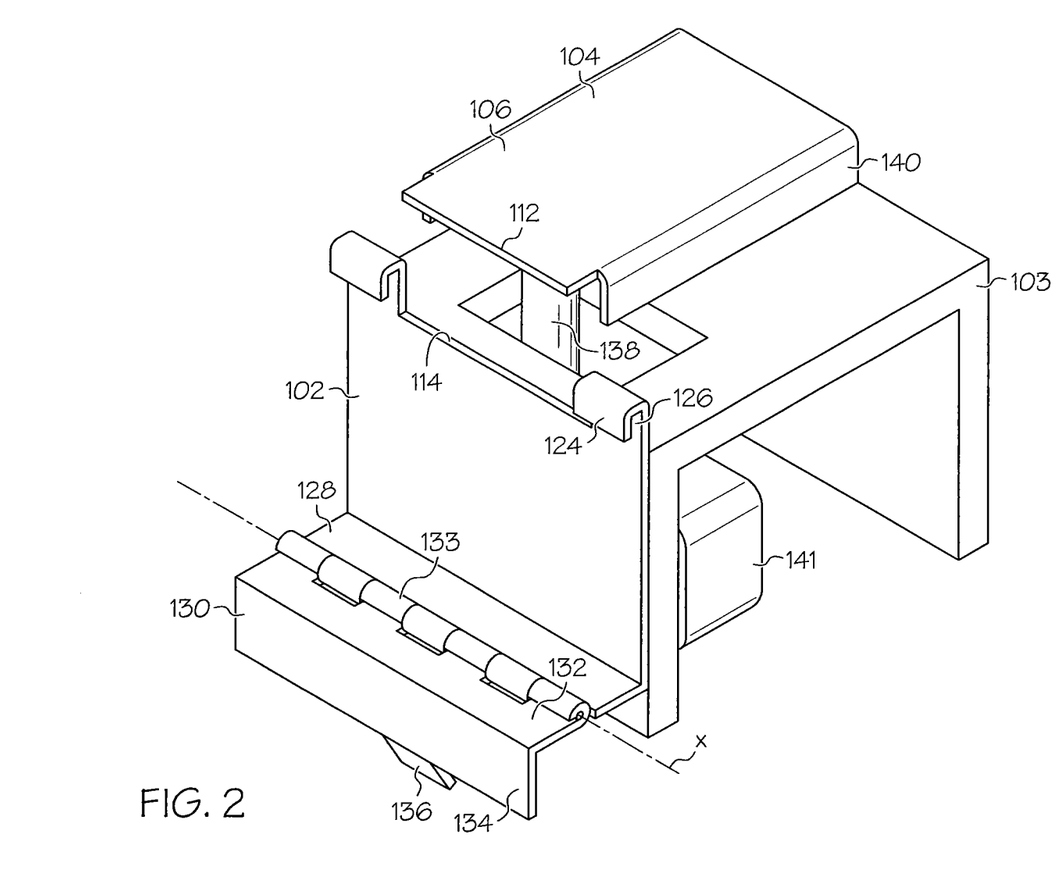
FIG. 2 is a front perspective view a platen tester in an open configuration.
Figure 3:
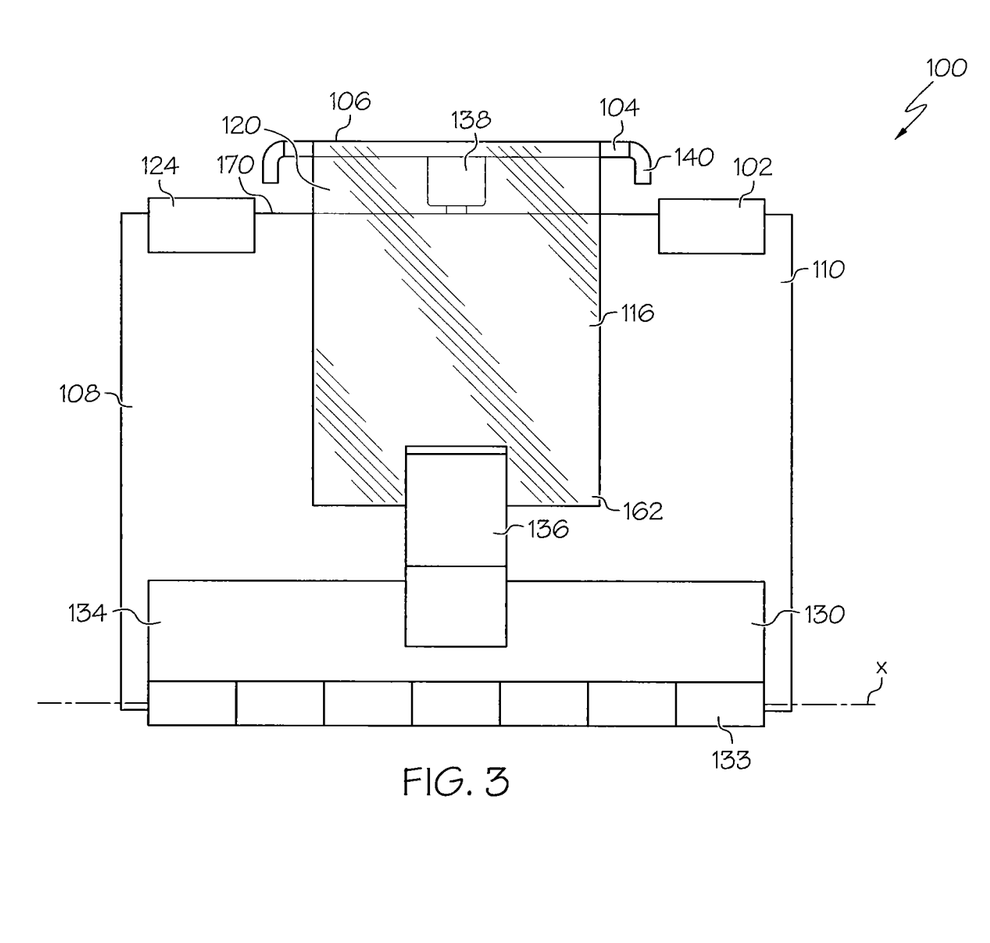
FIG. 3 is a front view of a platen tester containing a sample.
Figure 4:
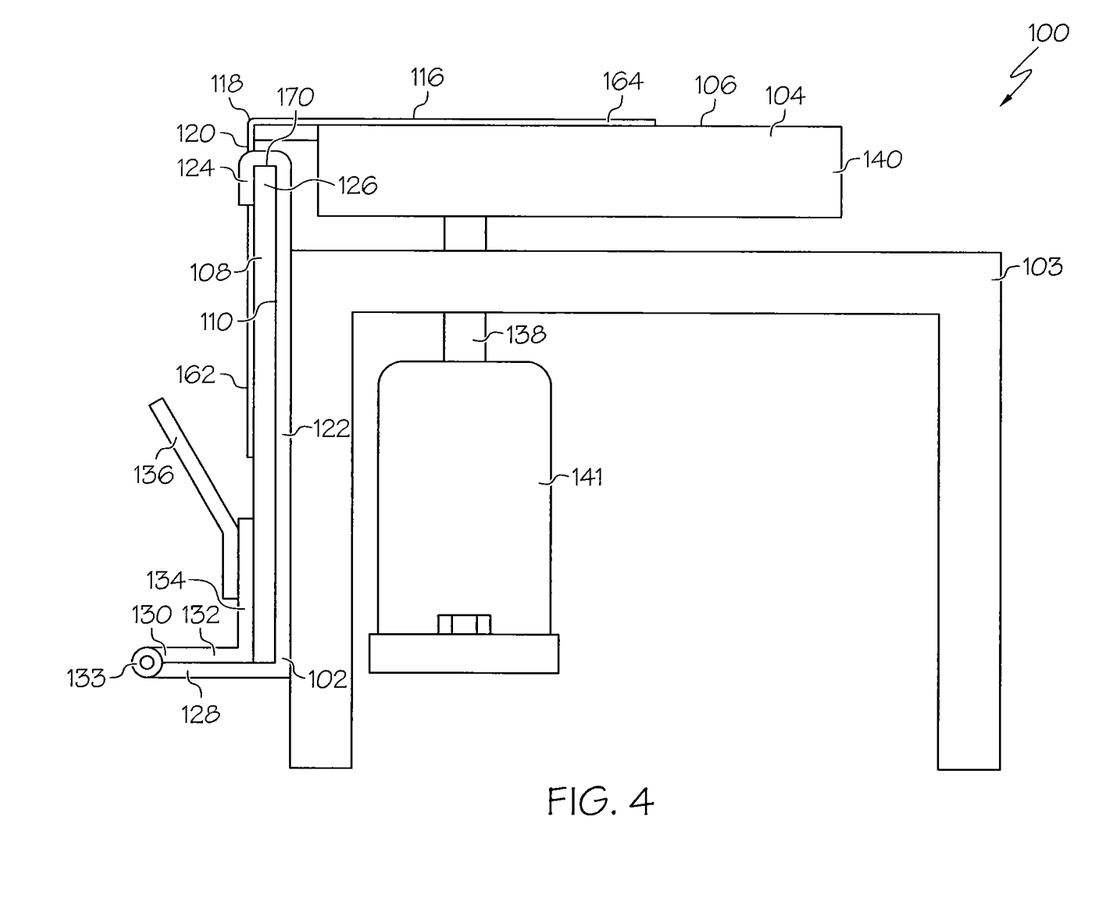
FIG. 4 is a side view of the platen tester of FIG. 3.

Referring now to FIGS. 2-4, platen tester 100 has a sample holder 102 and a moveable platen 104. Platen 104 has a major surface 106 in a first plane, and sample holder 102 is positioned to hold a sample of a substrate or adherend 108 in a second plane 110 substantially perpendicular to major surface 106 of platen 104. Platen 104 has a holder-proximate edge 112 adjacent to a platen-proximate edge 114 of sample holder 102. Edges 112, 114 may be substantially parallel to each other and spaced apart from each other. Sample holder 102 and platen 104 may both be attached to or positioned relative to a mounting structure 103 to maintain the relative positioning of sample holder 102 and platen 104. Sample 108 includes a section of adhesive tape 116 adhered thereto, and tape 116 extends beyond edge 114 of sample holder 102 and attaches to major surface 106 of platen 104, thereby forming an "L-clip" section 118 of tape 116. In one embodiment, there is a span 120 of tape 116 between sample 108 and platen 104 where tape 116 is not adhered to any surface.

Platen 104 and sample holder 102 are moveable with respect to each other in a direction substantially perpendicular to edges 112, 114, such that movement of platen 104 with respect to sample holder 102 separates edges 112, 114 from each other, but maintains their substantial parallelism. When platen 104 is moved relative to sample holder 102 while platen tester 100 contains a sample 108 of a substrate or adherend such as linerboard, with tape 116 attached to both sample 108 and platen 104, this relative movement applies a measurable load to tape 116 that can be analyzed to evaluate the strength of the adhesive bond of tape sample 116 to substrate or adherend sample 108. In the depicted embodiments of platen tester 100, moveable platen 104 is oriented generally horizontally, and sample holder 102 is oriented to hold sample 108 generally vertically. However, one skilled in the art will appreciate that platen 104 and sample holder 102 may be positioned in any spatial orientation so long as platen 104 and sample 108 are substantially perpendicular to each other as earlier described.

Referring now to an embodiment of sample holder 102, and still referring to FIGS. 2-4, sample holder 102 may include a generally flat mounting surface 122 substantially perpendicular to major surface 106 of platen 104. Thus, substrate sample 108 may be positioned substantially flat against mounting surface 122 to maintain sample 108 in the plane of sample holder 102 during testing. Sample holder 102 may have one or more spaced tabs 124 defining one or more slots 126, where slots 126 receive an edge of sample 108, and tabs 124 retain sample 108 in sample holder 102 during the operation of platen tester 100. Tabs 124 and slots 126 may be sized to retain a sample 108 with a particular width (e.g., ⅛ inch, ¼ inch, or ½ inch), or tabs 124 may include an adjustment mechanism (not shown) to vary the width of slots 126 to facilitate the use of sample holder 102 with samples 108 of different widths. Tabs 126 may be positioned on multiple edges of sample holder 102 to retain multiple edges of sample 108.

Sample holder 102 may include a retaining member 130. Retaining member 130 may be pivotal between an open position for sample loading (see FIG. 2) and a closed position for sample testing (see FIGS. 3-4). In the open position, retaining member 130 does not obstruct access to mounting surface 122, and thus sample 108 may be readily inserted within slots 126 and positioned flush against mounting surface 122. In the closed position, retaining member 130 secures sample 108 against mounting surface 122 thereby preventing dislocation of sample 108 during testing.

In one embodiment of retaining member 130, sample holder 102 includes a base or extension 128 that is generally perpendicular to mounting surface 122 and generally parallel with platen-proximate edge 114, and retaining member 130 is pivotally attached to base 128 via a hinge 133 (rotatable about axis x). Retaining member 130 may be generally "L" shaped, with a first portion 132 generally perpendicular to a second portion 134. To transition from the open position to the closed position, retaining member 130 rotates about axis x of hinge 133, which moves first portion 132 of retaining member 130 generally flush against and parallel with base 128 and moves second portion 134 of retaining member 130 into position generally parallel with mounting surface 122, thereby securing sample 108 between the generally parallel faces of second portion 134 of retaining member 130 and mounting surface 122. First portion 132 of retaining member 130 may be sized to ensure that in the closed position, the distance between second portion 134 and mounting surface 122 will be approximately equal to the width of slots 126 (or slightly less than the width of slots 126 to hold sample 108 more strongly). If tabs 124 are adjustable to vary the width of slots 126, base 128 or first portion 132 of retaining member 130 may be similarly adjustable to accommodate samples 108 of different sizes. Also, to better secure retaining member 130 in the closed position, base 128 and first portion 132 of retaining member 130 may include mateable features such as magnets, snaps, or other releasable attachment mechanisms. Retaining member 130 may also include a handle 136 to provide leverage to a user and assist in the transition between the open and closed positions.

One skilled in the art will appreciate that retaining member 130 may take any of a variety of different forms other than the described embodiment, so long as it is positionable to secure a sample 108 against mounting surface 122. For instance, retaining member 130 may be a clamp connected to sample holder 102 or mounting structure 103, a sliding mechanism along base 128, a magnet, a screw or nail that passes directly through sample 108, glue, adhesive, mateable releasable connectors (such as snaps, hook and loop connectors, etc.) affixed to mounting surface 122 and sample 108), and the like. Further, in embodiments including a hinge, hinge 133 may take any of a variety of forms known in the art consistent with the described functionality.

Referring now to an embodiment of platen 104 of platen tester 100, and still referring to FIGS. 2-4, platen 104 is supported by at least one actuator such as rod 138. Rod 138 is moveable to raise and lower major surface 106 of platen 104 relative to sample holder 102 such that edges 112, 114 remain substantially parallel to each other, yet the distance between edges 112, 114 varies. Rod 138 may be powered by actuator 141. Actuator 141 may be any component or device capable of applying the requisite force to raise major surface 106 of platen 104 for the purpose of applying a specified load to tape 116, such as a motor, a pneumatic or hydraulic pump, and the like. One skilled in the art will appreciate that other mechanisms besides rod 138 and actuator 141 may be used to raise and lower major surface 106 of platen 104 relative to sample holder 102 and apply a load without departing from the scope of this invention. For instance, platen 104 may be supported from above or from the side instead of from below and still maintain the requisite range of motion, or platen 104 may be stationary and sample holder 102 may be moveable to achieve the same net result.

Platen 104 may also include one or more spacer panel 140 generally perpendicular to major surface 106 to ensure the proper minimum spacing between major surface 106 and mounting structure 103. Spacer panels 140 may be on the sides of platen 104 (see FIGS. 2-4), and/or they may be attached to other portions of platen 104.

Figure 5:
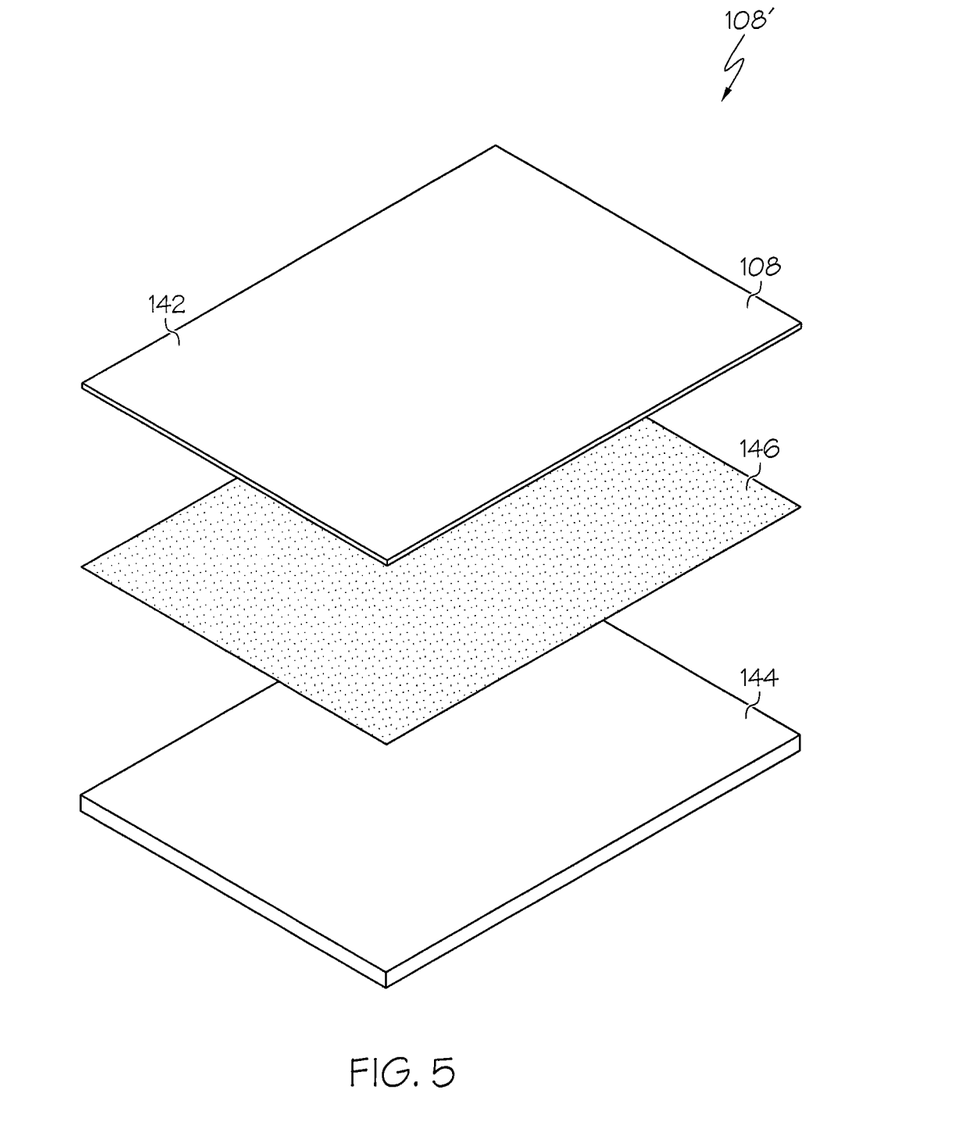
FIG. 5 is an exploded view of a linerboard sample.

Referring now to FIG. 5, sample 108 may take any of a wide variety of forms. In one embodiment, sample 108 is a generally rectangular piece of test material with dimensions of about four inches by three inches, but it should be understood that the specific shape and size of sample 108 is dictated by the size and shape of sample holder 102, which may take any of a wide variety of sizes and shapes without negatively impacting its function. Sample 108 may be cardboard, linerboard, plastic, metal, wood, or any other material to which the adhesion strength of tape 116 is to be tested. If sample 108 is sufficiently thick to fit in sample holder 102 (i.e. it has a thickness that is approximately equal to the width of slots 126), sample 108 may not require modification before insertion into sample holder 102. However, if sample 108 is too thin for direct testing, modification may be necessary. For example, a piece of linerboard 142 may be prepared for testing by attaching linerboard 142 to a piece of cardboard 144 of the appropriate thickness with double-sided tape 146 or by other appropriate attachment methods as known in the art.

Figure 6A:
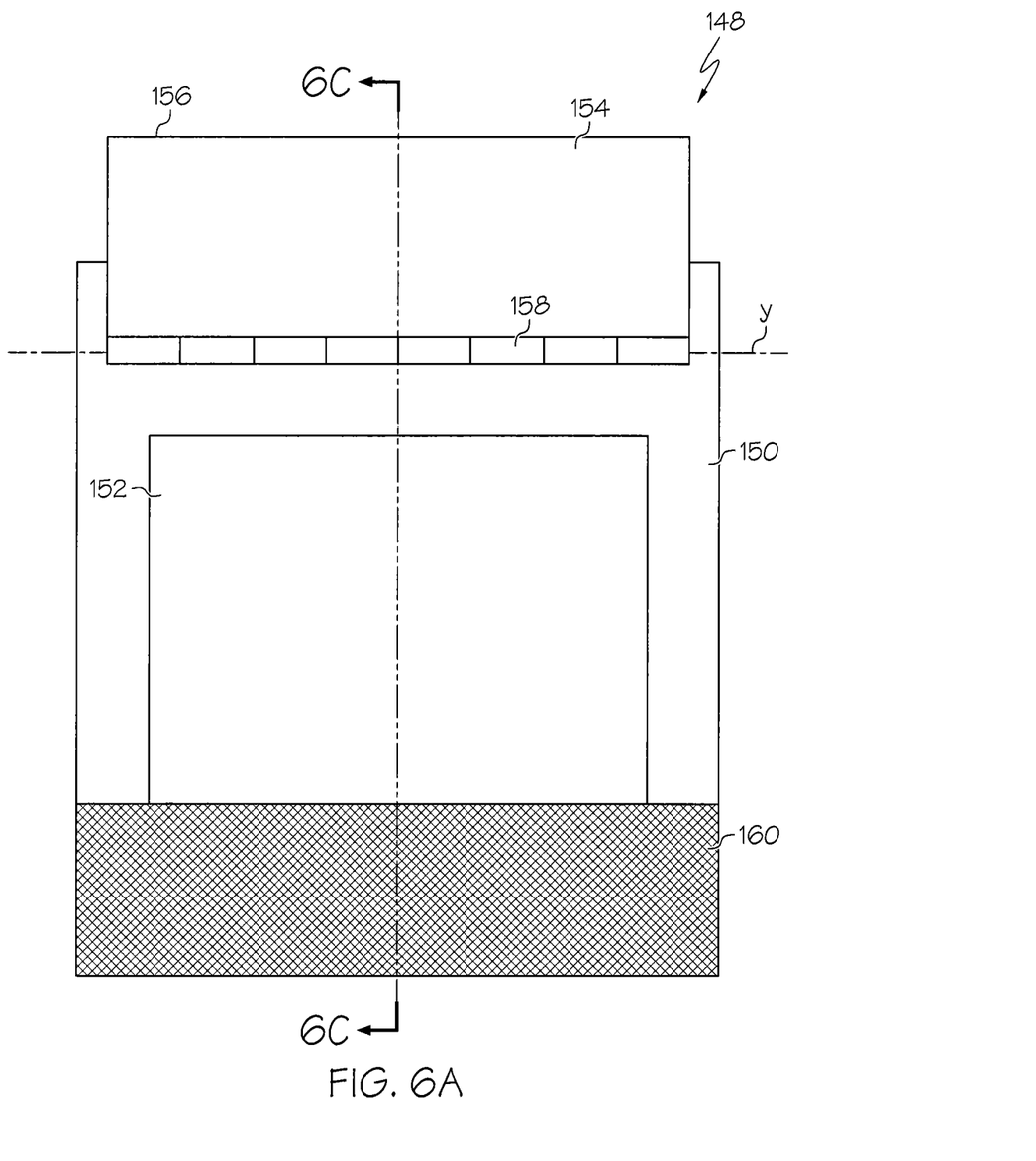
FIG. 6A is a top view of a jig in an open position.
Figure 6B:
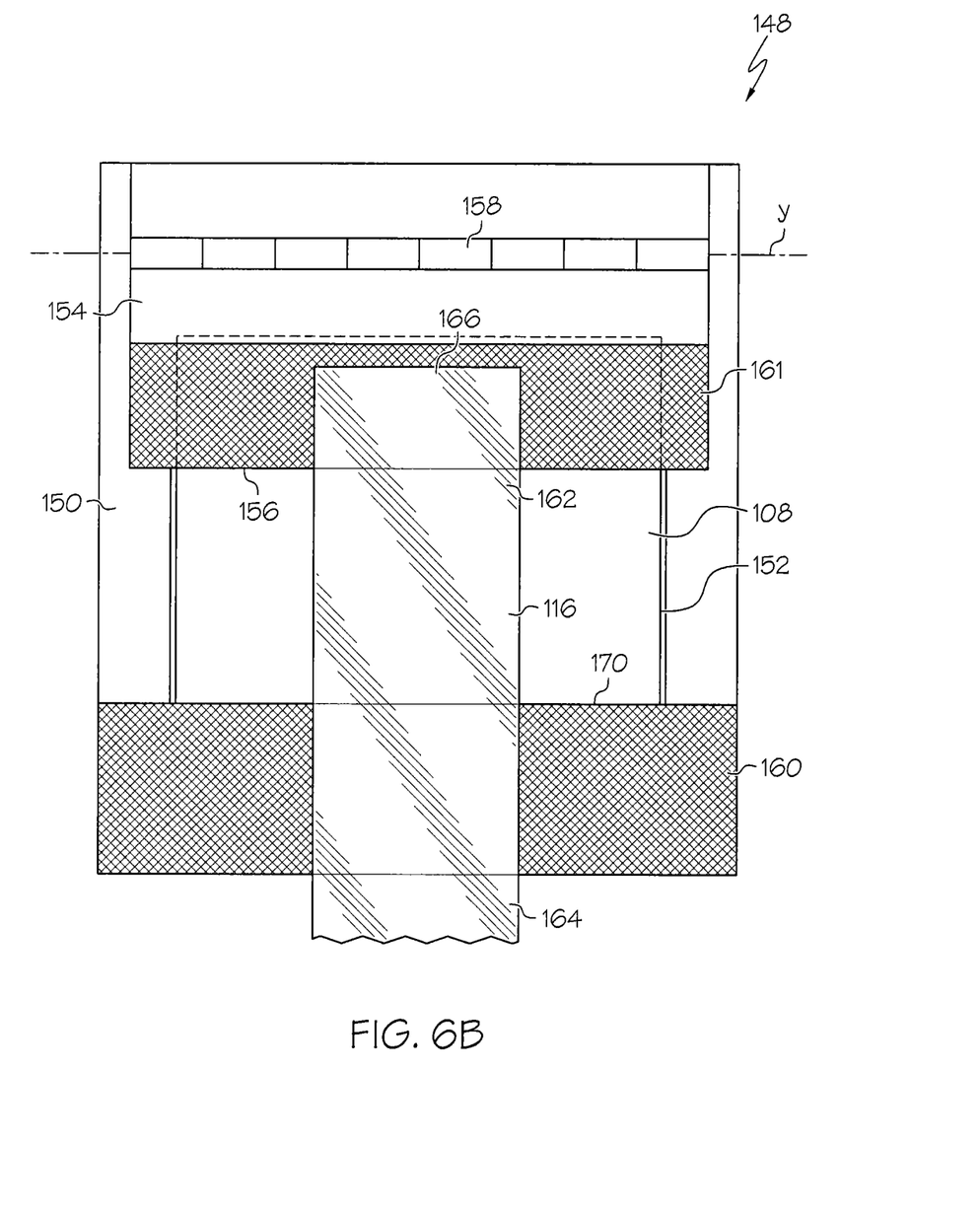
FIG. 6B is a top view of a jig in a closed position containing a sample.
Figure 6C:
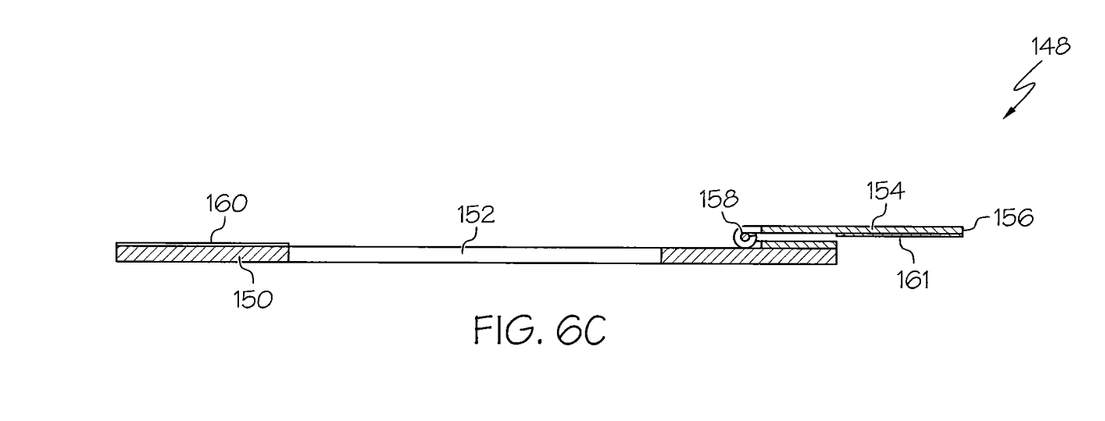
FIG. 6C is a side view of the jig of FIG. 6A taken along line 6C.
Figure 7:
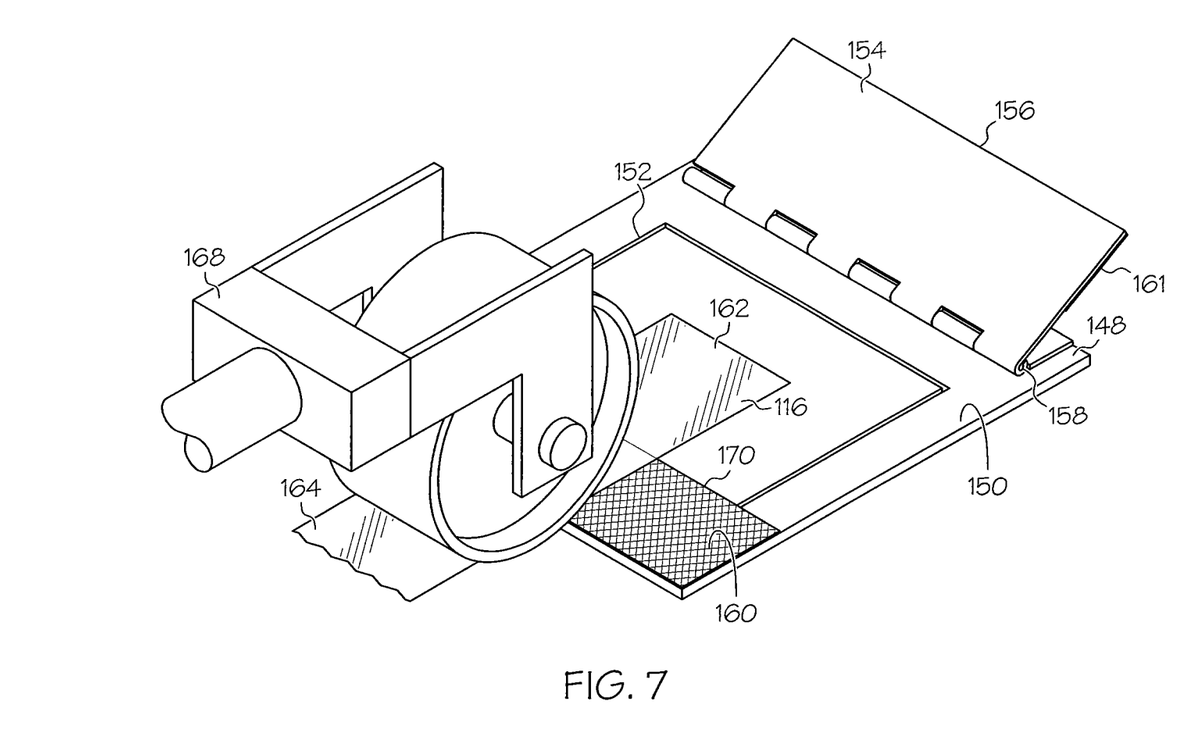
FIG. 7 is a front perspective view of a jig with a roller applying pressure to a sample.

Referring now to FIGS. 6-7, a jig 148 is disclosed for use in the preparation of sample 108 to facilitate the proper adherence of tape 116 to sample 108 to ensure that tape 116 is applied to a uniform surface area of each sample 108. In one embodiment, jig 148 is a generally flat, planar body 150 defining a frame 152 therein. Frame 152 is sized and shaped to contain sample 108, generally conforming with the dimensions of sample 108 (in one embodiment, four inches by three inches). Frame 152 may have a depth approximately equal to the thickness of sample 108, such that when sample 108 is inserted into frame 152, the surface of the jig 148/sample 108 complex is generally flat. Alternately, only a portion of the jig 148/sample 108 may be generally flat, for instance along only one edge of frame 152. Frame 152 may be a hole extending completely through body 150, or frame 152 may be a depression within body 150.

Jig 148 may have a flap 154 with an edge 156 positionable to overlay a pre-defined portion of frame 152. Flap 154 may span an entire edge of frame 152 as shown, or flap 154 may overlay only a portion of the width of frame 152. Flap 154 may be pivotally attached to body 150. In one embodiment, flap 154 is attached to body 150 via a hinge 158, and flap 154 is thus rotatable about axis y between an open position where flap 154 does not overlay frame 152 (FIGS. 6A, 6C, and 7) and a closed position where flap 154 does overly frame 152 (FIG. 6B). Jig body 150 and/or flap 154 may include release layers 160, 161 to which tape 116 will not strongly adhere.

With the basic structures of platen tester 100, sample 108, and jig 148 described, a method for preparing sample 108 with tape 116 and testing sample 108 using platen tester 100 will now be disclosed.

Still referring now to FIGS. 6-7, to apply tape 116 to sample 108, a sample 108 of the appropriate size is positioned within frame 152 of jig 148, with flap 154 in the open position (FIG. 6C). Flap 154 is then moved into the closed position such that flap 154 overlays sample 108 to the extent of edge 156 (in the embodiment of FIG. 6, flap 154 is pivoted about axis y to accomplish this). As shown in FIG. 6B, a length of tape 116 with a first, sample-contact end 162 and a second, platen-contact end 164 is applied to sample 108 and jig 148 generally perpendicular to edge 158 of flap 154. Second end 164 may extend beyond an edge 170 of sample 108 and, in one embodiment, beyond an outer edge of jig body 150 as well. Release layers 160, 161 should prevent tape 116 from strongly adhering to jig body 150 and flap 154. Tape 116 is cut at first end 162 along a line generally defined by edge 156 of flap 154, excising a segment 166 of tape 116 that overlays release layer 161 of flap 154 (segment 166 may be discarded). Thus, the pre-determined surface area of sample 108 covered by tape 116 is uniform for each sample 108 (assuming a constant width of tape 116), because edge 156 of flap 154 fairly precisely defines the positioning of first end 162 of tape 116 upon sample 108. Flap 154 is then returned to the open position, and tape 116 is pressed against sample 108, for example with a pressure roller 168, to apply a predetermined amount of pressure to tape 116 (e.g., 1, 2, 3, or 4 pounds). When tape 116 is adhered to sample 108, a portion of the length of tape 116 extending from release layer 160 is removed (defining the extent of second end 164), resulting in a segment of tape 116 of a predetermined size (e.g., two inches by six inches). Sample 108, with end 162 of tape 116 attached thereto and end 164 of tape 116 extending beyond edge 170, may then be removed from jig 148 for use with platen tester 100.

Referring back to FIGS. 2-4, with retaining member 130 in the open position, prepared sample 108 may be inserted into sample holder 102. Sample 108 should be oriented generally flat against mounting surface 122 with edge 170 received in slots 126 of tabs 124, and with free second end 164 of tape 116 extending beyond edge 114 of sample holder 102. Retaining member 130 may then be transitioned to the closed position, securing sample 108 in place as earlier described. Free second end 164 of tape 116 may then be guided past edge 114 of sample holder 102, past edge 112 of platen 104, and securely adhered (for instance, with the pressure of a user's fingers) to major surface 106 of platen 104, thereby defining "L-clip" section 118 of tape 116 between edges 112, 114. Testing of sample 108 may commence with the activation of rod actuator 141 to raise rod 138 to apply a predetermined load to tape 116 as earlier described, resulting in sheer tension between tape 116 and sample 108. As will be explained in more detail below, platen tester 100 may also include a timer 184 capable of automatically and contemporaneously measuring the time that elapses between applying the load to tape 116 and sample 108 and the time of failure.

Platen tester 100 may be used to collect various types of data pertaining to the strength of the adhesion between tape 116 and sample 108. In one case, a constant, predetermined load may be applied, and the time elapsed between the initial activation of platen tester 100 and the failure of sample 108 may be recorded. "Failure" occurs when tape 116 detaches at least partially from sample 108 because it lacks sufficient adhesive strength to resist the force of the load. In another case, a variable, increasing load may be applied, and the applied force strength at the moment of failure may be recorded. Or, a combination of these testing methods may be used.

For any of these methods, or other methods using platen tester 100, data may be compiled for various samples 108 using various tapes 116 with various loads, and the strengths and weaknesses of different combinations of samples 108 and tapes 116 may thus be quantitatively evaluated and compared. In addition to varying the load applied by actuator 141 to rod 138, other variables may be incorporated into the tests. For example, adhesion strength may be assessed at various temperatures and humidity levels to determine how a particular sample 108 functions in conjunction with a particular tape 116 at a particular temperature and humidity level (e.g., 35° F. with 25% relative humidity, 72° F. with 50% relative humidity, or 105° F. with 75% relative humidity). Thus, an array 10 of a plurality of platen testers 100 may be provided with the capability of performing the same or different tests simultaneously to accommodate more efficient comparative testing (and more accurate comparative testing in situations where room conditions are a factor).

Figure 8:
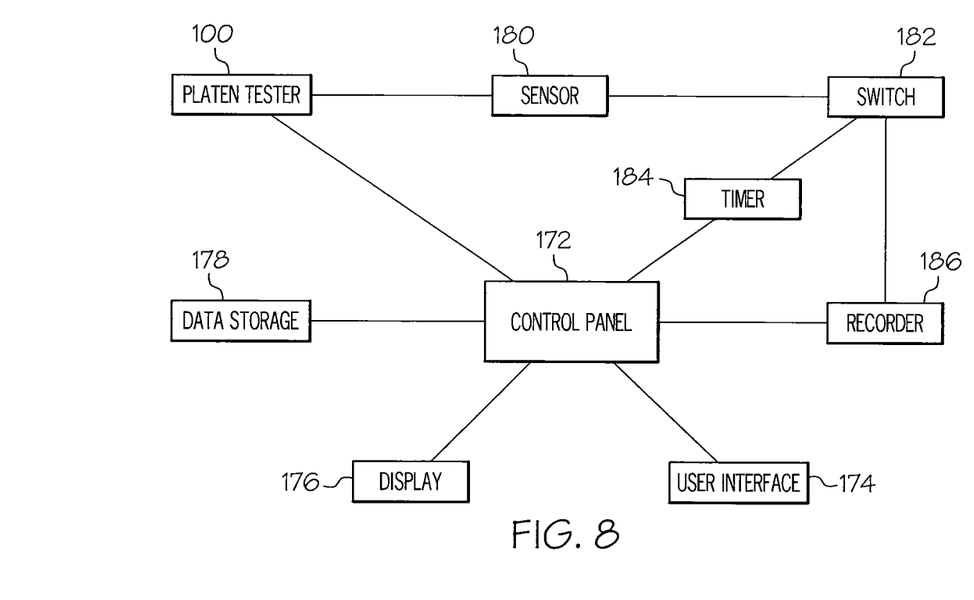
FIG. 8 is a schematic of the electronic components for use with a platen testing device.

Referring now to FIG. 8, platen tester 100 may be configured to communicate with other pieces of equipment to automate the testing and data recording process or to otherwise control the functionality of platen tester 100. For instance, platen tester 100 may be connected to a control panel 172 such as a computer. Control panel 172 may have a user interface 174 to input commands or settings for platen tester 100, such as the load to apply (e.g., two, four, six, eight, ten, or twelve pounds), the type of test to perform, the test duration, room attributes such as temperature and humidity, start and stop commands, and other functions pertinent to the use of platen tester 100. User interface 174 may be a keyboard, a touch screen, a voice activated control, or any other device capable of facilitating the transfer of information from a user to platen tester 100. Control panel 172 may also communicate with a display 176 to provide a visual representation of information related to all aspects and features of platen tester 100, including inputted commands and features, the status of tests currently underway (load information, testing time, etc.), completed tests (time to failure, etc.), and settings for future tests. Control panel 172 may also provide access to information stored in a data storage device 178 such as a hard drive, a portable flash drive, or the like, capable of storing test-related information. Control panel 172, user interface 174, display 176, and data storage device 178 may be separate components electrically connected by a wired or wireless connection, or two or more of these devices 172, 174, 176, 178 may be integrated into a single component performing two or more of the above-described functions. A single control panel 172 may be configured to communicate with multiple platen testers 100 in an array 10, separately or in tandem.

Platen tester 100 may include one or more sensors 180, such as a load cell, to detect the moment that a load is applied to sample 108 through actuation of platen 104, and also the moment of failure when tape 116 detaches from sample 108. Sensor 180 may link to a switch 182, which signals a timer 184 to begin timing at the moment of load application and to stop timing at the moment of failure. Switch 182 may be a physical component, or it may be a virtual switch. Switch 182 may also link to a recorder 186 capable of storing data related to the time to failure and/or the force of the load at the time of failure. Timer 184 and/or recorder 186 may be linked to control panel 172 to provide a user with access to information and settings related to timer 184 and/or recorder 186 via display 176.

As used in this specification and the claims to follow, when the word "substantially" is used to modify a term with a precise definition such as "planar," "perpendicular," "parallel," "equal," "flat," or the like, the modified term should be interpreted to include variations that differ in only minor respects from the precise definition, but nonetheless impress upon one skilled in the art the concept at issue. For instance, two lines may be "substantially perpendicular" if the two lines are within a few degrees of perpendicular. The term "generally" is similarly defined as a modifier, but with a slightly larger tolerance. Further, "generally" fully encompasses "substantially," such that, for example, if two lines are "substantially" parallel, they are also "generally" parallel.

Having described the invention in detail and with respect to specific embodiments thereof, it will be apparent that numerous modifications and variations are possible without departing from the spirit and scope of the invention as defined below.

What is claimed is:

1. A system for shear testing tape comprising:
   a sample holder comprising a mounting surface that defines a first plane, the mounting surface having a first edge; and
   a platen having a major surface that defines a second plane, the major surface having a second edge, wherein the second plane is perpendicular to the first plane, wherein the first edge is generally parallel to the second plane and the second edge is generally parallel to the first plane;
   wherein the platen is linearly movable relative to the sample holder in a direction parallel to the first plane such that the second edge moves parallel to the first plane or the sample holder is linearly movable relative to the platen in a direction parallel to the second plane such that the first edge moves parallel to the second plane, and wherein the first plane and the second plane remain perpendicular as the platen or the sample holder moves.

2. The system of claim 1, wherein the sample holder includes a retaining member that pivots between an open loading position and a closed testing position.

3. The system of claim 1, further including a plurality of additional devices for simultaneously testing a plurality of tapes under different loads and/or conditions.

4. The system of claim 1, wherein the mounting surface of the sample holder has a first edge and the major surface of the platen has a second edge, wherein the first edge is parallel and adjacent to the second edge.

5. The system of claim 1 further comprising a substrate sample and a length of tape, the length of tape having a first end and an opposite second end, wherein the first end of the length of tape is adhered to the substrate sample, wherein the substrate sample is received in the sample holder, and wherein the second end of the length of tape is adhered to the platen.

6. The system of claim 1, further comprising an actuator that linearly moves the platen relative to the sample holder.

7. The system of claim 6, wherein the mounting surface of the sample holder has a first edge and the major surface of the platen has a second edge, wherein the first edge is parallel and adjacent to the second edge, and wherein the first edge and the second edge remain parallel when the platen moves relative to the sample holder.

8. The system of claim 7, wherein the device further includes a control panel for selecting the force applied by the actuator.

9. The system of claim 1 further comprising an actuator operably coupled to the platen or the sample holder to move the platen or the sample holder, wherein the actuator is operable to apply variable amounts of force to move the platen or the sample holder.

10. A system for testing tape comprising
    a sample holder comprising a planar mounting surface for receiving a sample;
    a movable platen comprising an edge proximate to the planar mounting surface of the sample holder; and
    an actuator operatively coupled to the platen, wherein the actuator linearly translates the platen in a direction parallel to the planar mounting surface such that the edge of the movable platen translates parallel to the planar mounting surface of the sample holder.

11. The system of claim 10, wherein the movable platen comprises a major surface perpendicular to the planar mounting surface of the sample holder.

12. The system of claim 10, wherein the actuator is operable to apply variable amounts of force to linearly translate the platen.

13. The system of claim 10, wherein the edge of the platen is spaced away from the planar mounting surface of the sample holder.

14. A method for testing adhesion shear strength of a tape comprising the steps of:
    adhering a length of tape to a substrate sample, wherein an extension portion of the length of tape is positioned beyond an edge of the substrate sample;
    providing an adhesion shear strength testing system, the system comprising:
        a sample holder comprising a planar mounting surface;
        a movable platen comprising an edge proximate to the planar mounting surface of the sample holder; and
        an actuator operatively coupled to the platen, wherein the actuator linearly translates the platen in a direction parallel to the planar mounting surface;
    positioning the substrate sample in the sample holder of the adhesion strength testing device, wherein the extension portion of the length of tape is positioned proximate to the edge of the movable platen;
    adhering the extension portion of the tape to a surface of the movable platen; and
    actuating the platen to apply a load to the length of tape.

15. The method of claim 14, wherein the step of adhering the length of tape to the substrate sample is performed using a roller that applies a predetermined pressure to the tape as the tape is adhered to the substrate sample.

16. The method of claim 15, wherein the substrate sample is retained in a jig as the roller adheres the tape to the sample.

17. The method of claim 14, wherein a force of the load applied to the length of tape is varied over a period of time.

18. The method of claim 17, wherein the force of the load is increased at intervals or continuously until the length of tape at least partially detaches from the sample.

19. The method of claim 14, wherein a force of the load applied to the length of tape is constant over a period of time.

20. The method of claim 14, further comprising monitoring temperature, humidity, or temperature and humidity.

* * * * *